United States Patent [19]

Ferguson

[11] Patent Number: 5,784,193
[45] Date of Patent: Jul. 21, 1998

[54] MICROSCOPE SLIDE WITH REMOVABLE LAYER AND METHOD

[76] Inventor: Gary W. Ferguson, 4806 Fernglen Drive, Burnaby, B.C., Canada, V5G 3V7

[21] Appl. No.: 673,326

[22] Filed: Jun. 28, 1996

[51] Int. Cl.$^6$ .......................... G01N 21/01; G01B 21/34
[52] U.S. Cl. ..................... 359/398; 359/396; 435/288.4
[58] Field of Search ............................ 359/391–398; 356/244, 246; 422/51, 58–60, 101–104; 435/288.3, 288.4, 305.1, 305.2

[56] References Cited

U.S. PATENT DOCUMENTS

| | | | |
|---|---|---|---|
| 3,551,023 | 12/1970 | Brackett | 156/60 |
| 3,843,452 | 10/1974 | Freake et al. | 435/287.8 |
| 3,922,464 | 11/1975 | Silver et al. | 428/355 AC |
| 4,032,237 | 6/1977 | Jolesz | 356/244 |
| 4,190,314 | 2/1980 | Goldsmith | 359/397 |
| 4,250,830 | 2/1981 | Leif | 118/52 |
| 4,299,920 | 11/1981 | Peters | 435/288.4 |
| 4,441,793 | 4/1984 | Elkins | 359/398 |
| 4,556,297 | 12/1985 | Schulz, Jr. | 359/397 |
| 4,682,891 | 7/1987 | de Macario et al. | 356/244 |
| 5,170,285 | 12/1992 | Shibasaki | 359/396 |
| 5,358,692 | 10/1994 | Reynolds | 422/104 |
| 5,571,721 | 11/1996 | Turner | 359/398 |

FOREIGN PATENT DOCUMENTS

| | | | |
|---|---|---|---|
| 47210 | 10/1972 | Netherlands | 435/288.4 |

OTHER PUBLICATIONS

Schenk U: "Quality Assurance by Continuous Recording of the Microscope Status," *Acta Cytologica*, 40:73–80 (Jan.–Feb. 1996).

Zahniser DJ, Sullivan PJ: "CYTYC Corporation," *Acta Cytologica*, 40:37–44 (Jan.–Feb. 1996).

Knesel, "Roche Image Analysis Systems, Inc.," Acta Cytologica vol. 40, No. 1, pp. 60–66.

McGoogan & Reith, "Would Monolayers Provide More Representative Samples and Improved Preparations for Cervical Screening?", Acta Cytologica vol. 40, No. 1, pp. 107–119.

Grohs et al., "AccuMed International, Inc." Acta Cytologica vol. 40, No. 1, pp. 26–30.

Kamentsky et al., "CompuCyte Corporation," Acta Cytologica vol. 40, No. 1, pp. 31–36.

Berger, "Statistical Quality Assurance in Cytology" Acta Cytologica vol. 40, No. 1, pp. 97–106.

Vooijs et al., "Cytosafe™" Acta Cytologica vol. 40, No. 1, pp. 90–96.

Patten et al., "NeoPath, Inc.," Acta Cytologica vol. 40, No. 1, pp. 45–52.

Mango, "Neuromedical Systems, Inc." Acta Cytologica vol. 40, No. 1, pp. 53–59.

(List continued on next page.)

*Primary Examiner*—Thong Nguyen
*Attorney, Agent, or Firm*—Kolisch, Hartwell, Dickinson, McCormack & Heuser

[57] ABSTRACT

A slide for depositing for observation material under a microscope comprising a mounting surface to receive material for observation and a removable layer on the mounting surface formed with at least one opening in the removable layer to define at least one exposed region on the mounting surface for retaining material to be observed when the removable layer is detached. The exposed region has definite boundaries and any material to be examined remaining on the slide is confined to the exposed region to facilitate examination of the slide by human visual identification or machine vision by making material easier to locate, by limiting material to regions appropriate for best observation (e.g. away from edges of the slide and coverglass), and by limiting the amount of material or area covered by material to permit quick and rigorous observation and analysis. A method for using slides according to the present invention is also disclosed.

10 Claims, 3 Drawing Sheets

OTHER PUBLICATIONS

Wilbur et al., "Sensitivity of the AutoPap 300 QC System for Cervical Cytologic Abnormalities," Acta Cytologica vol. 40, No. 1, pp. 127–132.

Sprenger et al., "The False Negative Rate in Cervical Cytology," Acta Cytologica vol. 40, No. 1, pp. 81–89.

Rosenthal et al., "Computer–Assisted Rescreening of Clinically Important False Negative Cervical Smears Using the PAPNET Testing System," Acta Cytologica vol. 40, No. 1, pp. 120–126.

ASCT News, vol. XVI, No. 3, 1995.

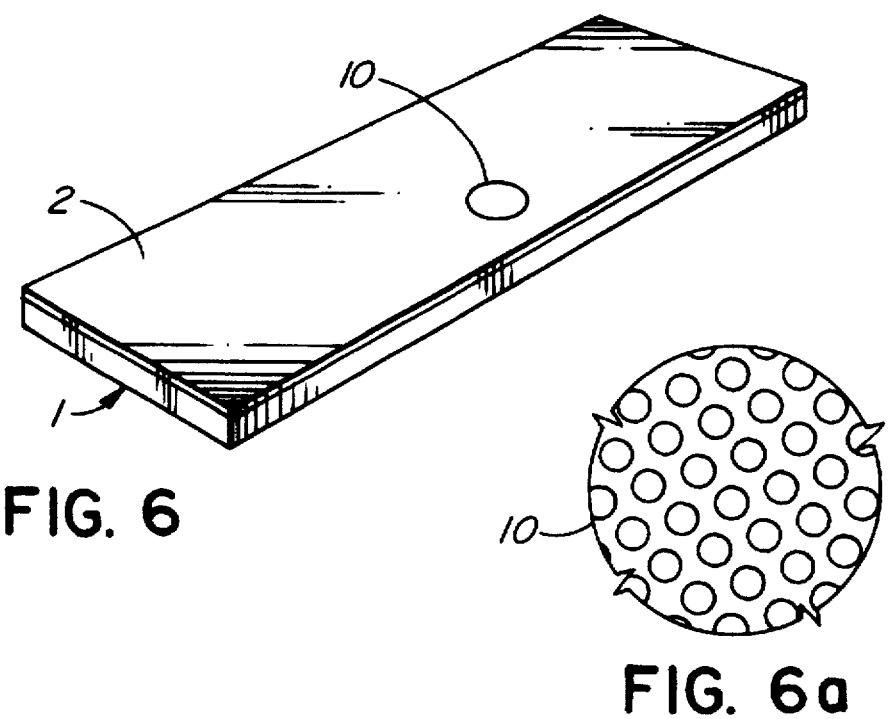
FIG. 6
FIG. 6a
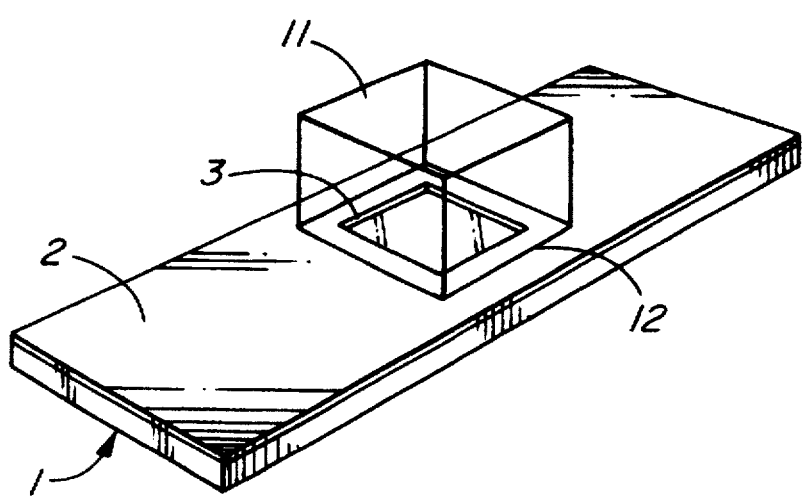
FIG. 7

MICROSCOPE SLIDE WITH REMOVABLE LAYER AND METHOD

FIELD OF THE INVENTION

This invention relates generally to an apparatus and method useful in the field of microscopy. More particularly, the invention relates to a slide having a removable surface layer with at least one exposed region on the slide such that when the surface layer is removed, material to be examined remains on the slide and is confined to the exposed region(s) of the slide.

BACKGROUND OF THE INVENTION

Biological cells and other materials are routinely mounted on slides and examined with the aid of a microscope. Stains are usually employed in some manner to enhance the visibility of cells or cell components such as specific proteins, amino acids or DNA. In general these sample assessments seek to locate and identify cells with abnormal characteristics. Diagnosis of biological samples is typically accomplished by human visual identification, although machine vision alone or machines which provide additional quantitative measurements are gaining acceptance to assist with what is often an arduous task.

The ability to efficiently examine and diagnose samples on slides is influenced by a large number of factors including the following:

(i) Restricting material placement on the slide;

(ii) Treating the sample to achieve optimal viewing;

(iii) Observing all or the vast majority of material on the slide.

The advantages of restricting sample material placement on a slide include but are not limited to:

(i) material is easy to locate;

(ii) material is limited to regions appropriate for best observation (e.g. away from edges of the slide and coverglass);

(iii) the amount of material or area covered by material is limited to facilitate quick and rigorous observation and analysis.

If sample material is restricted to specific regions of the slide, it is much easier to establish with some confidence that all the material present was viewed by either human or machine vision or both. In some applications (e.g. clinical use as a medical device) the ability to make these direct comparisons may be essential in obtaining appropriate device approvals and/or establishing the required confidence to broadly adopt use of the device within medical practice. Experts in the field of applied machine vision will have a full appreciation of these factors.

In conventional use, material for examination under a microscope is routinely deposited on a microscope slide by smearing, blotting or some method of sedimentation from fluid suspensions, often using a centrifuge. Conventional methods of making slides recognize the need to (i) increase the adherence of material to the slide; (ii) increase the desired composition of the sample (e.g. the desired number and or type of cells present); (iii) improve the presentation of material (e.g. spread material out, ideally in a single focal plane, while reducing obscuration due to overlapping material); (iv) improve the consistency of the presentation of material; (iv) capture material on another device and then bind this device or otherwise transfer the desired material to the slide; (v) restrict material for viewing to permanent wells or defined regions of the slide; and (vi) ensure that the sample material (e.g. cells) deposited on the slide is a true and representative sample (e.g. of the organ or tissue site) for the intended use.

In general, material deposited using conventional methods may by intent or by accidental contact, appear anywhere on the surface of the slide. Although some sample deposition methods, such as blotting material previously captured on a circular filter, do provide some control over the region, these methods do not restrict the placement of sample material. Accidental transfer of material beyond the original region may easily occur as slides undergo subsequent handling, staining or other common sample processing steps.

Restricting the placement of material on a slide is not fully addressed in the prior art.

U.S. Pat. No. 3,551,023 to Brackett discloses a laminated specimen holder which is used for tissue samples and sandwiches material between two thin films, however, material does not contact the slide surface and this invention specifically suggests not using a microscope slide for this purpose.

Goldsmith in U.S Pat. No. 4,190,314 acknowledges that observation of all the material on the slide is necessary to detect cancerous cells, if present, even in very low numbers. Goldsmith provided a series of grid lines to help direct user observation along defined grid paths. This method suffers from the disadvantage that the lines can obscure some subtle cellular details and has limited scope because observations on an individual sample often require the use of more than one objective lens.

Current microscope based system design may use 'electronic grid lines' providing users with slide tracking information as users perform slide scanning. A pictorial or other indicator related to the scanning process is provided by the microscope system and may be accompanied by 'electronic marking' (remembering x,y stage coordinates and perhaps information on the objective lens and focus position) of important areas for more detailed or subsequent review. Alternatively, microscope systems may employ a computer driven stage under full or interactive user control to scan the slide surface in a pre-defined manner, however, it is still necessary to know the boundaries of the sample region so that a pre-defined pattern over the region can be established with confidence.

Even if the region boundaries are known and all regions of the slide are visited, abnormal cells may still fail to be observed due to overlapping material or optical changes which may occur at the edges of the slide and coverglass. The problem of overlapping material is recognized in the field and techniques have been developed to reduce this in a number of ways. One approach is to prepare a uniform thin layer of sample material from a fluid suspension utilizing density centrifugation, centrifical methods or otherwise blotting cells first captured on a filter.

U.S. Pat. No. 5,170,285 to Shibasaki describes a semitransparent slide that scatters light emitted from a microscope to optically eliminate the outline of pores of a filter medium included in the configuration. The slide surface is non-removable and the implementation does not restrict the placement of specimen material.

Machine vision systems, some of which employ neural networks, along with others that make measurements on the spatial distribution of DNA in cell nuclei have performance that depends on properly observing all, or the vast majority of cells or cellular material, present on the slide.

The need to observe all cells for maximum detection sensitivity has been recognized, and is true for both humans and machines. Achieving this objective is becoming more important as machine vision gains acceptance in both interactive and automated roles in sample screening. Even in cases where adequate machine performance is achieved by looking at a subset of the cells present, increased statistical accuracy and higher confidence is achieved by observing all, or the vast majority of cells present. A number of barriers serve to limit the acceptance of machines for cell analysis. Some of these include user acceptance based on performance, and confidence. In addition, substantiating performance claims by clinical trials is also necessary for medical regulatory approvals in many countries. For machine vision to be effectively employed, in most instances it is desirable to know where the boundaries of the region(s) of interest are, restrict the size of the region(s) to practical dimensions commensurate with the technology and time available for analysis, restrict material to areas with consistent optical properties and to provide confidence that material is not present on areas beyond the desired region(s). The ability to limit the placement of material to specific regions on a slide means it is much easier to establish with some confidence that all the material present will be viewed using machine vision.

In many applications, including but not limited to clinical samples, the material present on the slide serves as a permanent and enforceable record. Developments in many instances strive to ensure that material to be examined is a true and representative sample of the material of interest (e.g. organ or tissue site). In the case of diagnostic medicine, few unobserved or incorrectly identified cells of significance may alter the interpretation or, in cases of error, may allow disease to go untreated, exposing the testing laboratory to significant risk and perhaps forming the basis of a litigious process. Unobserved cells may result from overlapping material, non-uniform, large amounts or wide dispersion of material. It may be difficult to consistently observe every field of the slide when the region of interest is large or when material is present in areas which are not best for observation (e.g. near edges of the slide or coverglass where optical properties may vary markedly).

SUMMARY OF THE INVENTION

In view of the foregoing, there is a need for a microscope slide arrangement that addresses the limitations of the prior art, particularly with respect to the desired feature of restricting material placement on the slide to specific regions.

Applicant has developed a slide and a method for making a slide in which the material deposited on the slide is easily and reliably confined to a specific region.

Accordingly, in a first aspect the present invention provides a slide for observing material under a microscope comprising:

a mounting surface to receive material for observation;

a removable layer on the mounting surface formed with at least one opening in the removable layer to define at least one exposed region on the mounting surface for retaining material to be observed when the removable layer is detached.

In a further aspect, the present invention provides a method for preparing a microscope slide that includes a removable layer formed with at least one opening therein defining at least one exposed region on the mounting surface of the slide comprising the steps of:

processing and fixing material to be observed on the mounting surface of the slide over the removable layer and the opening therein; and removing the removable layer from the mounting surface to create at least one region on the mounting surface that retains material to be observed within set boundaries defined by the at least one opening.

In a still further aspect, the present invention provides a method for preparing a microscope slide comprising the steps of:

applying a removable layer formed with at least one opening therein to the slide to define at least one exposed region on the mounting surface of the slide comprising the steps of:

processing and fixing material to be observed on the mounting surface of the slide over the removable layer and the opening therein; and removing the removable layer from the mounting surface to create at least one region on the mounting surface that retains material to be observed within set boundaries defined by the at least one opening.

The apparatus and method of the present invention provide a slide having the following desirable properties:

(i) material is restricted to a defined region of the slide (ii) the shape and dimensions of the defined region are controlled, and (iii) multiple regions can be provided on the slide.

The foregoing properties provide increased confidence that material on the slide does not appear beyond the desired region(s) of the slide.

The slide and method of the present invention provide the following potential advantages:

The device can be used with many existing cell deposition methods including:

Smears, touch preps, blotting and thin layer techniques.

The device allows some sample treatment steps prior to removal of the surface layer potentially reducing stain or other requirements.

The device acts as a temporary reaction chamber to facilitate sample treatment prior to the removal of the surface layer.

The device allows material to be restricted to regions of convenient shapes and sizes.

The device protects from the accidental placement of sample material outside of the desired region(s).

The device increases productivity by restricting material to a designated area of the slide for faster locating by both human and machine vision.

The device serves an active role in cell preparation by carrying stain or influencing the sample before it contacts the region of interest.

The device is used to restrict material away from edges of the slide or coverglass to reduce or eliminate these optical interferences.

The device makes it practical to observe all or the vast majority of material present on the slide by restricting the amount, area and location available for material.

The device provides increased confidence that material does not appear outside of the restricted region.

The device itself facilitates the production of a disperse sample for some uses by providing a plurality of small regions.

The device makes it practical to have several of the same or different samples on the same slide. These sample regions may or may not be treated in the same manner.

DESCRIPTION OF THE DRAWINGS

Aspects of the present invention are illustrated, merely by way of example, in the accompanying drawings in which:

FIG. 6 is a perspective view of another slide embodiment having a removable layer formed with a plurality of small openings to assist in dispersion of sample material; and FIG. 7 shows a slide according to the present invention supporting a cuvette of sample material sealed to the removable layer which acts as a gasket over the opening in the layer.

DESCRIPTION OF THE PREFERRED EMBODIMENTS

Figure 1:
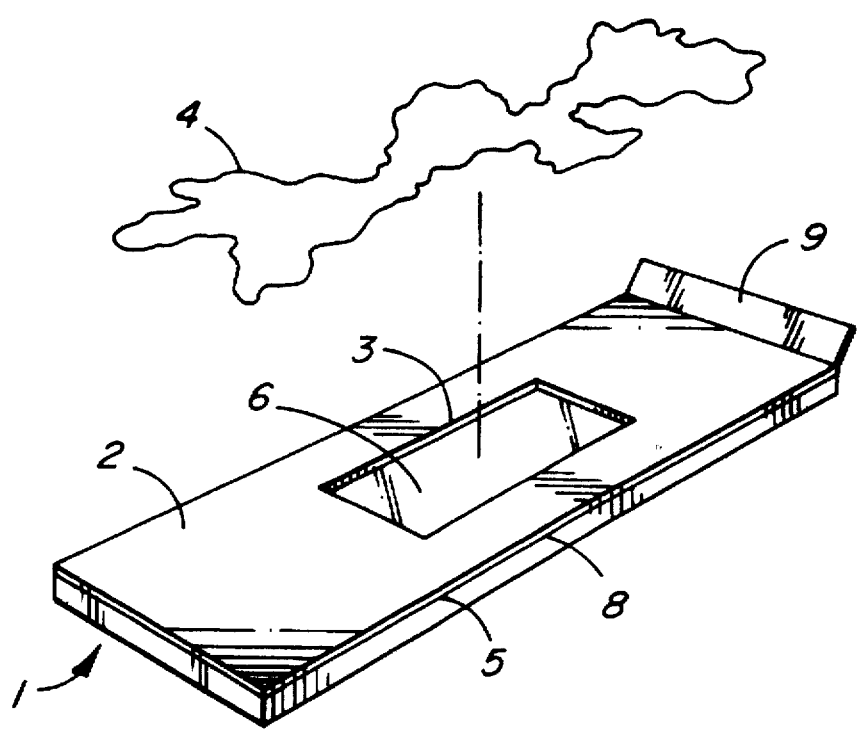
FIG. 1 is a perspective view of a preferred embodiment of a slide according to the present invention with a removable surface layer having at least one exposed region.

Referring to FIG. 1, there is shown a microscope slide 1 for observing material under a microscope according to a preferred embodiment of the present invention. The slide comprises a mounting surface 5 in the form of a conventional glass slide having a removable surface layer 2 applied thereto. Removable layer 2 is formed with an opening 3 to define an exposed region 6 on mounting surface 5 for retaining material 4 to be observed.

Figure 2:
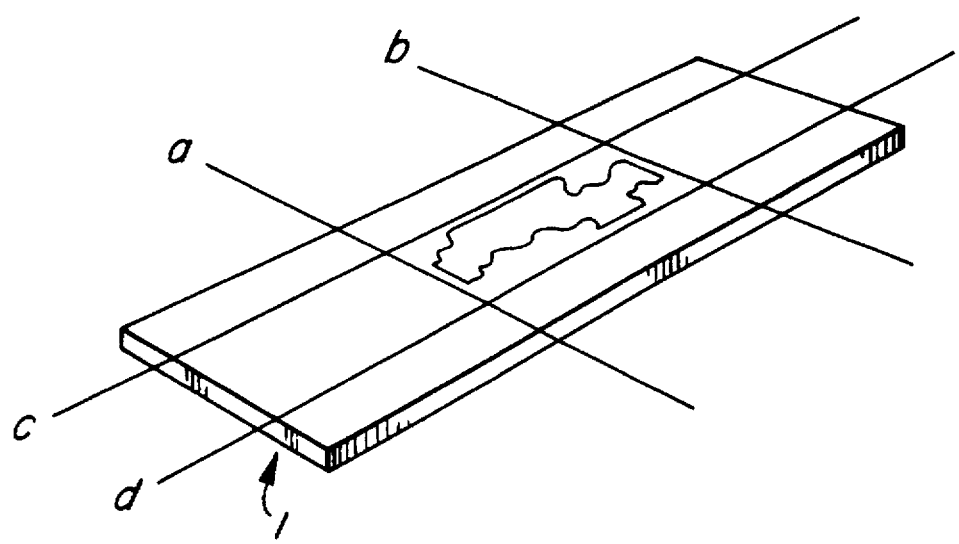
FIG. 2 shows a perspective view of the slide with the surface layer removed.

In use, material 4 to be observed under a microscope is deposited in an appropriate manner on the slide of the present invention in the general area of opening 3 in removable layer 2. The sample material is processed and fixed on the mounting surface of the slide over the removable layer and the opening therein. Removable layer 2 is then detached from mounting surface 5 by pulling on tab 9. As a consequence of removing layer 2, sample material 4 to be observed remains on mounting surface 5 only in the region 6 defined by opening 3 to create a region having definite boundaries. The area of the slide to be examined in detail extends beyond the border of exposed region 6 as indicated by lines a-b-c-d in FIG. 2. A region of desired dimensions can be selected to best suit a particular application. Areas of the slide which may be difficult to observe (e.g. edges of the slide or coverglass which could have undesirable optical properties) can be avoided.

Figure 4:
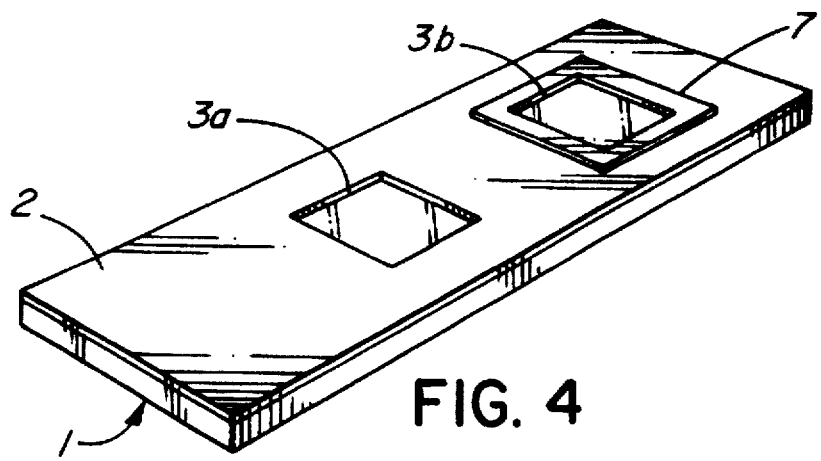
FIG. 4 shows a perspective view of another slide according to the present invention.

FIG. 4 illustrates an alternative embodiment of the slide of the present invention in which removable layer 2 is formed with a pair of openings 3a and 3b. The number and dimensions of such openings can be selected as desired. A plurality of openings in layer 2 provide for a slide having a plurality of discrete, spaced openings to define a plurality of exposed regions on the mounting surface when the removable layer is detached.

Figure 5:
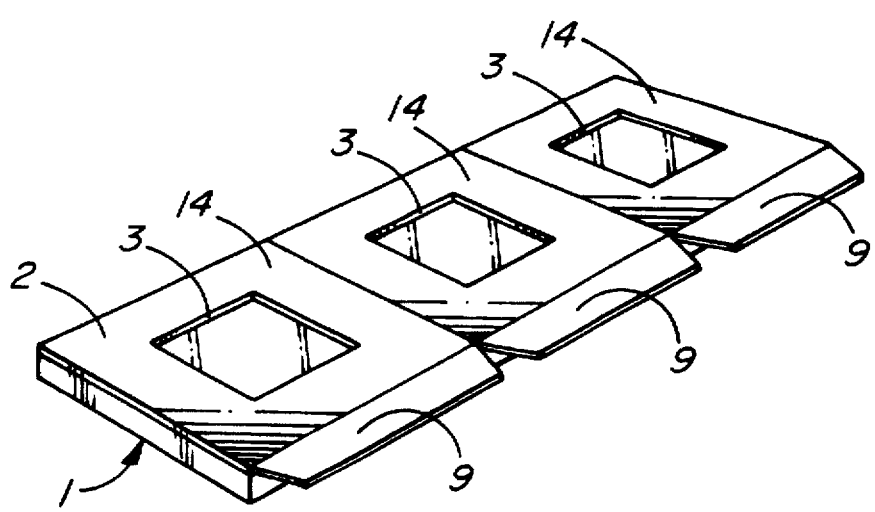
FIG. 5 is a perspective view of a further slide embodiment having a plurality of separate removable layers that are removable independently of each other.

In a further embodiment shown in FIG. 5, removable layer 2 is divided into multiple portions 14. Each portion is detachable from the mounting layer independently of the other portions and is formed with at least one opening 3. This arrangement allows different sample treatment steps such as staining to be carried out on the samples and potentially reduces reagent requirements and hence reagent costs by virtue of the fact that the entire slide does not need to be treated only the region defined by each opening 3. Opening 3 also acts as a well to receive and contain stains or other reagents to the region of the sample material.

Individual and independent treatment, particularly by staining, of each opening 3 also has the advantage that cross-contamination of slides and samples is avoided. Conventional slides are often treated by immersing batches of slides in a bath of reagent. The bath of shared or reused reagent can lead to cross-contamination of slides as material is transferred from a first slide to the bath and then on to a second slide.

FIG. 6 illustrates a further embodiment in which removable layer 2 is formed with a multitude of microscopic openings as shown in enlarged view 10. When cellular material is deposited on the slide and layer 2 removed, the microscopic openings will act to create a dispersed array of cellular specimens on the slide.

In all embodiments, removable layer 2 preferably comprises a sheet of flexible material having an adhesive surface 8 to removably attach the removable layer to mounting surface 5. The sheet of flexible material is formed with a non-adhesive gripping tab 9 to facilitate removal from the mounting surface. Tab 9 is preferably an overlapping end of the removable layer 2 (with the exposed adhesive covered) to provide a simple, consistent gripping point to peel away the removable layer like a tape strip.

Several options were evaluated to determine an effective removable layer 5. Evaporation methods were tested and demonstrated that thin layers could be created on the surface of the slide, exposing a region, however, these lacked some of the desired properties outlined above and required a drying step. Advances in materials may make these viable options in the future.

It is preferable that the removable layer is formed from materials having one or more of the following properties:

(i) the material is relatively easy to remove from the mounting layer, (ii) possible damage to the removable layer can be observed, (iii) the removable layer is resistant to drying and is resilient to a wide range of environmental factors such as heat and moisture, (iv) the removable layer can withstand a wide range of routine sample treatment steps which may be employed before removing the layer, (v) the slide is not damaged by the removal of the removable layer, (vi) removal of the removable layer has little or no effect on the sample material left behind in the exposed region, (vii) removing the removable layer leaves little or no residue on mounting surface 5.

The adhesive material for removable layer 2 is preferably selected from a distinct category of adhesives often referred to as "pressure-sensitive". These adhesives are characterized by what has been termed a "four-fold balance" of adhesion, cohesion, stretchiness and elasticity. The pressure sensitive adhesive should satisfy the requirements stated above which include no or little residue transfer, resistance to drying, stability over a range of temperatures and resistance to some sample processing steps.

A wide range of suitable pressure-sensitive adhesives are available. Some common types include synthetic rubber (providing controlled properties) tackified with some type of resinous material also known as rubber-resin adhesive. These can be formulated so as not to permit adhesion buildup. In general, there are advantages to using newer wholly synthetic pressure-sensitive adhesives since their behaviour is predictable and can be controlled making them more suitable for manufactured products. Silver in U.S. Pat.

No. 3,922,464 issued Nov. 25, 1975 describes an adhesive sheet material that employs a pressure-sensitive adhesive that make it removable from a wide variety of surfaces. The material comprises a self-sustaining backing which is coated with a stable viscous copolymer latex formed from monomers of (1) major amounts of alkyl acrylates (2) minor amounts of certain emulsifier monomers and (3) if desired, minor amounts of zwitterionic monomers. The water is evaporated from the latex to leave a tacky pressure-sensitive adhesive. 3M Corporation and others have a wide range of sheet-like products which employ pressure-sensitive adhesives which are suitable to implement the basic removable layer of the present invention.

Removable layer 2 is preferably opaque so that it is easy to observe its presence, its removal and any damage. In addition, this surface layer can be color coded to identify slides for specific applications with potentially different surface layer compositions.

The removable layer described preferably has some inherent elastic properties owing to the material of the layer, its thickness and the adhesive on the self adhesive side.

The removable surface layer described can function as a gasket as illustrated in FIG. 7. Cells in fluid suspension are often deposited onto the surface of a microscope slide via sedimentation or under increased gravitational force achieved by centrifuging. FIG. 7 shows an open sample tube or cuvette 11 pressed against removable layer 2 about opening 3 to form a seal 12. For use in such an application, removable layer 2 is formed with additional adhesives or includes a groove cut into layer 2 to receive and seal the edges of the sample tube 11. Alternatively, layer 2 can include a rubber-like coating of appropriate thickness to receive the sample tube. The foregoing arrangements eliminates the need for a separate gasket that is necessary with conventional slides.

Figure 3:
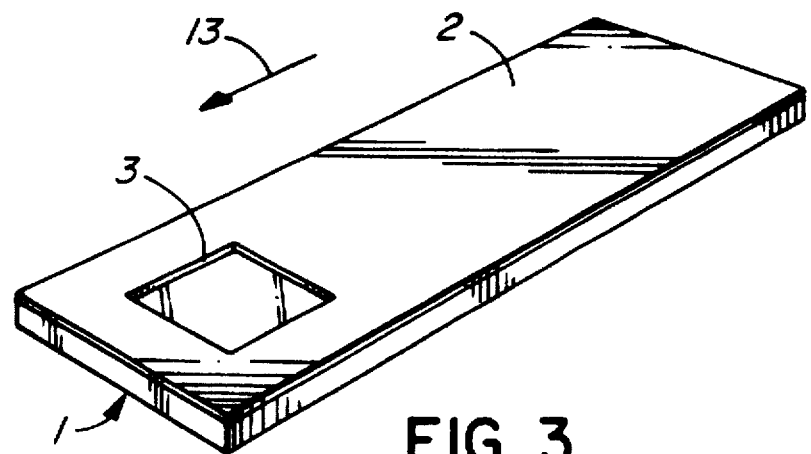
FIG. 3 is a perspective view of an alternative embodiment of a slide according to the present invention.

In addition to the above beneficial properties, removable layer 2 can be designed and selected to have other useful properties. Three examples of these properties are as follows:

(i) The removable layer can include on or as a part of the layer a substance selected to interact with the material to be observed. The removable layer can be coated with a substance which interacts with the sample material in a desired way, perhaps staining or selectively effecting the concentration of the material that eventually contacts the exposed area of the slide. To expand on this theme with a specific example, FIG. 3 illustrates a slide having a removable cover layer coated with a protein which preferentially binds to one type of cell. The protein is employed as a component of the removable layer 2 to remove some undesired cells. Sample material containing a mixed population of cells A and B (e.g. maternal blood containing fetal cells) at concentrations of 998 cells per thousand cells and 2 cells per thousand, respectively, is applied to the removable surface 2. The slide is tilted allowing the sample material to flow to opening 3 in the direction of arrow 13 over the protein, selectively binding and removing some of the undesired material or cells while unbound material continues to move toward opening 3. The resulting concentration of the desired cells (e.g. fetal cells) is higher (e.g. 20 cells per thousand) in the resulting sample material deposited on mounting surface 5 within opening 3.

(ii) The removable surface layer is designed such that it can also function as a gasket allowing a seal to be made to facilitate the centrifical deposition of sample material on the desired region(s) of the slide.

(iii) The slide of FIG. 4 is useful for preparing and treating the same material differently on the same slide. Sample material (e.g. cells) in exposed regions 3a and 3b (FIG. 4) is first treated in some manner (e.g. DNA stained). Region 3b is then sealed with a temporary covering material 7, allowing an additional processing step (e.g. Pap staining) to be applied to the sample material in region 3a. The temporary covering material is then removed and the samples analyzed.

Although the present invention has been described in some detail by way of example for purposes of clarity and understanding, it will be apparent that certain changes and modifications may be practised within the scope of the appended claims.

I claim:

1. A slide for depositing material for observation under a microscope comprising:

a mounting surface to receive material for observation;

a removable layer on the mounting surface formed with at least one opening in the removable layer, the removable layer and the at least one opening being adapted to receive material for observation such that detachment of the layer from the mounting surface removes material deposited on the layer and the mounting surface retains material to be observed only in the at least one exposed region on the mounting surface defined by the at least one opening in the removable layer.

2. A slide as claimed in claim 1 in which the removable layer is formed with a plurality of discrete, spaced openings to define a plurality of exposed regions on the mounting surface.

3. A slide as claimed in claim 1 in which the removable layer is divided into multiple portions, each portion being detachable from the mounting layer independently of other portions and being formed with at least one opening.

4. A slide as claimed in claim 1 in which the removable layer comprises a sheet of flexible material having an adhesive surface to removably attach the removable layer to the mounting surface.

5. A slide as claimed in claim 4 in which the sheet of flexible material is formed with a non-adhesive gripping tab to facilitate removal from the mounting surface.

6. A slide as claimed in claim 1 in which the removable layer is opaque.

7. A slide as claimed in claim 1 in which the removable layer is coated with a substance selected to interact with the material to be observed.

8. In a slide for depositing material for observation under a microscope, the improvement comprising a removable layer attachable to the slide, the removable layer being formed with at least one opening therethrough to define at least one exposed region on the slide for retaining material to be observed when the removable layer is detached from the slide to remove material that is outside the at least one exposed region.

9. A method for preparing a microscope slide having a mounting surface on which material is deposited and that includes a removable layer formed with at least one opening therein defining at least one exposed region on the mounting surface comprising the steps of:

processing and fixing material to be observed on the mounting surface of the slide over the removable layer and the opening therein; and removing the removable layer from the mounting surface to create at least one region on the mounting surface that retains material to be observed within set boundaries defined by the at least one opening.

10. A method for preparing a microscope slide having a mounting surface on which material is deposited comprising the steps of:

applying a removable layer formed with at least one opening therein to the slide to define at least one exposed region on the mounting surface of the slide;

processing and fixing material to be observed on the mounting surface of the slide over the removable layer and the opening therein; and removing the removable layer from the mounting surface to create at least one region on the mounting surface that retains material to be observed within set boundaries defined by the at least one opening.

* * * * *